US009291595B2

(12) United States Patent
Bae et al.

(10) Patent No.: US 9,291,595 B2
(45) Date of Patent: Mar. 22, 2016

(54) MONITORING METHOD AND SYSTEM OF METAL IONS OR OXYGEN IONS APPLICABLE TO HIGH CONCENTRATION NON-AQUEOUS ELECTROLYTE

(71) Applicants: Korea Atomic Energy Research Institute, Daejeon (KR); Korea Hydro & Nuclear Power Co., Ltd., Gyeongsangbuk-Do (KR)

(72) Inventors: Sang Eun Bae, Sejong-Si (KR); Kyuseok Song, Daejeon (KR); Dae Hyeon Kim, Daejeon (KR); Yong Joon Park, Daejeon (KR); Jong Yun Kim, Daejeon (KR); Jei Won Yeon, Daejeon (KR)

(73) Assignees: KOREA ATOMIC ENERGY RESEARCH INSTITUTE, Daejeon (KR); KOREA HYDRO & NUCLEAR POWER CO., LTD., Gyeongsangbuk-Do (KR)

( * ) Notice: Subject to any disclaimer, the term of this patent is extended or adjusted under 35 U.S.C. 154(b) by 660 days.

(21) Appl. No.: 13/797,401

(22) Filed: Mar. 12, 2013

(65) Prior Publication Data

US 2013/0264222 A1 Oct. 10, 2013

(30) Foreign Application Priority Data

Mar. 14, 2012 (KR) ........................ 10-2012-0026282

(51) Int. Cl.
*G01N 27/411* (2006.01)
*G01N 27/416* (2006.01)
*G01N 27/48* (2006.01)

(52) U.S. Cl.
CPC .......... *G01N 27/4166* (2013.01); *G01N 27/416* (2013.01); *G01N 27/4118* (2013.01); *G01N 27/48* (2013.01)

(58) Field of Classification Search
CPC G01N 27/411; G01N 27/4118; G01N 27/416
See application file for complete search history.

(56) References Cited

U.S. PATENT DOCUMENTS 5,139,626 A 8/1992 Yamaguchi et al.
7,390,392 B1 6/2008 Choi et al.
(Continued)

FOREIGN PATENT DOCUMENTS

CN 1403804 3/2003
CN 1912610 2/2007
(Continued)

OTHER PUBLICATIONS

Ogura et al., "Dissolution of Cathode Nickel in Molten Carbonates I. In-situ Measurement of Dissolved Ni2+ Concentration by Means of Anodic Stripping Method," Denki Kaga oyobi Kogyo Butsuri Kagaku (1987), 55(5), 392-5.*
(Continued)

*Primary Examiner* — Alexander Noguerola
(74) *Attorney, Agent, or Firm* — Morrison & Foerster LLP

(57) ABSTRACT

A monitoring method of metal ions or oxygen ions applicable to a high concentration non-aqueous electrolyte includes: applying a potential in a non-aqueous electrolyte to obtain current information with respect to the potential; varying the potential applied in the non-aqueous electrolyte containing metal ion concentration or oxygen ion concentration such that the metal ion concentration or the oxygen ion concentration is maintained in spite of the potential being applied; detecting a linear relationship among the concentration, the current, and passed charges in the non-aqueous electrolyte by repeatedly performing the obtaining step and the varying step, while changing the concentration; and calculating metal ion concentration or oxygen ion concentration of the non-aqueous electrolyte in pyroprocessing of the non-aqueous electrolyte by using the linear relationship. Concentration and components of a solute existing in a non-aqueous electrolyte can be measured while an electrowinning process and pyroprocessing is being conducted.

20 Claims, 16 Drawing Sheets

(56) References Cited

U.S. PATENT DOCUMENTS

2007/0034530 A1     2/2007    Lin et al.
2011/0156722 A1     6/2011    Nebling et al.

FOREIGN PATENT DOCUMENTS

| | | | |
|---|---|---|---|
| CN | 102057273 | 5/2011 | |
| JP | 2005-17173 A * | 1/2005 | ............. G01N 27/41 |
| KR | 100992890 | 11/2010 | |

OTHER PUBLICATIONS

The definition for "anodic stripping voltammetry" in the Oxford Dictionary of Biochemistry and Molecular Biology (2 ed.), 1998.*

JPO computer-generated English language translation of Osaka et al. JP 2005-17173 A, patent published Jan. 20, 2005.*

Mugikura et al. "Meniscus Behavior of Metals and Oxides in Molten Carbonate under Oxidant and Reducing Atmospheres: I. Contact Angle and Electrolyte Displacement," J. Electrochem. Soc. vol. 143, No. 8, Aug. 1995.*

Hong et al., "Wetting Characteristics of Carbonate Melts under MCFC Operating Conditions," Journal of The Electrochemical Society, 151 (1) A77-A84 (2004).*

Iizuka et al. (2001) "Application of Normal Pulse Voltammetry to On-Line Monitoring of Actinide Concentrations in Molten Salt Electrolyte," Journal of Nuclear Materials 297:43-51.

Johnson et al. (2006) "On-Line Monitoring of Actinide Concentrations in Molten Salt Electrolyte," ANS 2006 Winter Meeting (INL/CON-06-11515 Preprint).

Office Action in Chinese Patent Application No. 10201310080529.4, issued Aug. 8, 2014, 9 pages.

* cited by examiner

MONITORING METHOD AND SYSTEM OF METAL IONS OR OXYGEN IONS APPLICABLE TO HIGH CONCENTRATION NON-AQUEOUS ELECTROLYTE

CROSS-REFERENCE TO RELATED APPLICATION

Pursuant to 35 U.S.C. §119(a), this application claims the benefit of earlier filing date and right of priority to Korean Application No. 10-2012-0026282, filed on Mar. 14, 2012, the contents of which is incorporated by reference herein in its entirety.

BACKGROUND OF THE INVENTION

1. Field of the Invention

The present disclosure relates to a method and system for measuring a concentration of a non-aqueous electrolyte in an eletrowinning process of metal and pyroprocessing of spent nuclear fuel.

2. Background of the Invention

Spent nuclear fuel made in a nuclear power plant includes a significant amount of high-level wastes as well as a large amount of unreactive uranium. In order to recycle unreacted uranium and reduce the volume of high-level wastes, recently, pyroprocessing has been highlighted. Pyroprocessing includes an electrolytic-reduction process, an electrolytic-refining process, and an electrowinning process. The crux of these processes is melting spent nuclear fuel in molten salt, electrochemically reducing respective elements such as uranium, trans-uranium, and the like, and electrodepositing and recovering the same on a cathode.

The pyroprocessing recovers uranium and trans-uranium (TRU) elements from molten salts, so it is critical to accurately measure components and concentration of uranium and trans-uranium elements existing in molten salt in carrying out the respective processes such as electrolyte refining, electrowinning Conventionally, components and concentration of uranium and trans-uranium elements are measured by sampling (or collecting) molten salt by using an analysis technique such as inductively coupled plasma atomic emission spectroscopy (ICP-AES) or inductively coupled plasma mass spectrometer (ICP-MS), but in order to smoothly carry out the process, real-time monitoring solute concentration of molten salt having a relatively high temperature on the spot is urgently required.

Real-time monitoring method required for pyroprocessing may be classified into two fields.

A first method is a spectroscopic measurement method devised to allow absorption spectroscopy, laser-induced fluorescence spectroscopy, or the like, to be applied to pyroprocessing. The spectroscopic method mainly uses a light source, a measurement cell, and a detector, and has an advantage in that a characteristic signal according to an element can be detected, but disadvantageous in that it is difficult to install these components in a molten salt cell having a high temperature of pyroprocessing.

A second measurement is a method of applying an electrochemical measurement method to real-time monitoring. This measurement method is a method of measuring a type and amount of a solute existing in molten salt having a high temperature by measuring an electrochemical signal, i.e., a current signal. Since a process system is configured as an electrochemical system, the electrochemical measurement method is expected to be easily applied to a process cell. Electrochemical measurement methods known so far include a normal pulse voltammetry, a square wave voltammetry, and the like. With these methods, when a reaction of a solute existing in an electrode/solution interface is measured by repeating electrodeposition and dissolution reactions in a manner of scanning while applying pulses, the solute existing in a bulk of the solution is drawn to the electrode interface due to a diffusing phenomenon to increase concentration of the solute to the electrode/solution interface, having shortcomings in that a proportional relationship is not obtained in high concentration of 4 wt % or higher. Also, in case of using a conventional cyclic voltammetry or chronoamperomery, an excessive amount of electrodeposits are formed simultaneously with an electrodeposition reaction to rapidly increase an electrode area, having a problem in measuring a solute of high concentration. Besides, with the measurement methods, rough concentration of spent nuclear fuel in the molten salt having a high temperature can be measured, but since a potential scan time is protracted, lengthening a measurement time, and reduction potential is not appropriate for analyzing neighboring elements. In addition, molten salt having a high temperature is in a very highly harsh environment, so many materials are not stable in the molten salt having a high temperature, and when an electrode is put in the molten salt having a high temperature, a surface of the molten salt having a high temperature rises, changing a contact area of the electrode. In order to constantly maintain an electrode area, a method of wraping (or covering) the electrode with an insulator may be used, but when a potential of a reduced area is applied to the alumina used as an insulator within the molten salt having a high temperature, the alumina, or the like, is reduced to an aluminum metal so as to be changed into a conductor in quality, disadvantageously increasing the electrode area. Besides, in performing an electrochemical measurement on the solute of high concentration in the non-aqueous solution, if the electrode area is large, a middle portion of the electrode is cavitated of solute ions during the electrochemical measurement. Thus, the electrochemical measurement of the solute of high concentration by using an electrode having a large area cause a certain area of the electrode to be incapacitated, resulting in that a value lower than a current proportional to high concentration is measured.

Also, concentration measurements of oxygen anions have been performed by using an electrochemical method such as cyclic voltammetry, square wave voltammetry (SWV), or the like. These methods use a reaction of oxidizing oxygen anions to evolve oxygen. However, while a reaction current is being measured, oxygen continues to be produced, and to cling to an electrode surface, which induces the electrode area decreasing.

As a process of refining metal ores existing in nature, electrolytic refining process is commonly performed in a non-aqueous solution. Metal ores include a metal oxide as a combination of metal and oxygen, and during an electrolytic refining process, metal cations are reduced at a cathode to electroseparate metal so as to be recovered, and oxygen anions are oxidized at an anode to generate oxygen. In this process, the metal electrolytic reduction reaction occurs based on a principle similar to that of the pyroprocessing. Thus, the metal ore refining process also urgently requires a real-time measurement method for measuring elements refined in a non-aqueous solution in real time, in order to monitor an ongoing situation of the process.

SUMMARY OF THE INVENTION

Therefore, an aspect of the detailed description is to provide a method and system for monitoring concentration of metal ions and oxygen ions in a non-aqueous solution in real time during a metal electrolytic refining process and pyroprocessing.

To achieve these and other advantages and in accordance with the purpose of this specification, as embodied and broadly described herein, a measuring apparatus for monitoring non-aqueous metal ions of 4 wt % or greater in real time, including: one electrode forming a meniscus on a surface of a non-aqueous solution including a solute therein through a port formed in an upper portion of a processing device; another electrode estimating a height of the one electrode to form the meniscus of the electrode; an adjusting device installed in the port operated to adjust the height of the two electrodes; a potentiostat measuring potentials and currents of the two electrodes and adjusting the same; and a protective cover protecting the meniscus formed on the two electrodes.

In an example in relation to the present invention, in the measuring apparatus for monitoring non-aqueous metal ions in real time, an electrode connected to a wire having a size equal to or less than 1 mm as a means for maintaining an electrode area in the non-aqueous solution constantly is put in a non-aqueous solution, to thereby minimize a relative electrode change.

In an example in relation to the present invention, in the measuring apparatus for monitoring non-aqueous metal ions in real time, MgO and BeO which are not reactive in a potential window of the non-aqueous electrolyte as a means for maintaining an electrode area in the non-aqueous solution constantly is used as an insulator covering the electrode, to thereby minimize a change in the electrode without a reaction of the insulator.

In an example in relation to the present invention, in a monitoring method of metal ions, a reduction potential may be applied to a working electrode in a non-aqueous electrolyte for three seconds to measure a reduction current of only a solute existing in an electrode/solution interface with respect to the potential, and the deposited metal may be dissolved to extract only concentration information of the solute existing in the vicinity of the electrode/solution interface, and concentration (enrichment) of solute ions on the interface can be prevented.

In an example in relation to the present invention, in a monitoring method for monitoring oxygen ions, an oxidation potential may be applied to a working electrode in a non-aqueous electrolyte for three seconds to measure an oxidation current of only a solute existing in the electrode/solution interface with respect to the potential and may be reduced or stopped to prevent a generation of oxygen bubbles generated on a surface of the electrode to extract only concentration information of oxygen ions existing in the vicinity of the electrode/solution interface.

In an example in relation to the present invention, a monitoring method of metal ions or oxygen ions may include: applying a reduction (metal ions) potential or an oxidation (oxygen ions) potential to a non-aqueous electrolyte for within three seconds to obtain information regarding a reduction current or an oxidation current; varying the potential applied in metal ion concentration or oxygen ion concentration of the non-aqueous electrolyte such that the metal ion concentration or the oxygen ion concentration is maintained in spite of the potential being applied; detecting a linear relationship among the concentration, the current, and passed chargepassed charges in the non-aqueous electrolyte by repeatedly performing the obtaining step and the varying step, while changing the concentration; and calculating metal ion concentration or oxygen ion concentration of the non-aqueous electrolyte in pyroprocessing of the non-aqueous electrolyte by using the linear relationship.

In an example in relation to the present invention, a reduction potential and an oxidation potential may be repeatedly applied to a working electrode in the non-aqueous electrolyte in the obtaining step and the varying step. The reduction potential and the oxidation potential having a constant magnitude may be applied to a working electrode in the non-aqueous electrolyte, respectively, and the monitoring method may include relatively lengthening a period of time during which the oxidation potential is applied to diffuse the dissolved metal ions from the electrode/solution interface to a bulk of the solution.

In an example in relation to the present invention, in the obtaining step and the varying step, a potential maintaining a constant magnitude may be applied to a working electrode in the non-aqueous electrolyte, while decreasing and increasing the potential by stages (or stepwise), in order to sequentially generate a reduction current and an oxidation current.

In another example in relation to the present invention, in the obtaining step and the varying step, a potential having a reducible magnitude may be applied to a working electrode in the non-aqueous electrolyte to precipitate the metal ions, and thereafter, the potential may be increased to electrochemically dissolve the metal films.

In another example in relation to the present invention, a working electrode, a counter electrode, and a reference electrode of a potentiostat may be put in the non-aqueous electrolyte in order to obtain current information with respect to the potential. In order to maintain cleanliness, a positive pulse potential may be further applied periodically to the working electrode. In order to prevent the working electrode from being incapacitated due to a large area, the working area may have a size ranging from 1 $nm^2$ to 0.5 $cm^2$.

Also, a monitoring apparatus and method of metal ions and oxygen ions including: applying a potential to a non-aqueous electrolyte, while changing concentration of a solute in the non-aqueous electrolyte, to obtain a correlation of a current with the potential in each concentration, by using any one of a repeating redox method in which a period is repeated by changing a reduction-oxidation direction of a potential, a multi-step redox method in which a potential is changed by stages, and a redox scanning method in which a potential is changed from a potential in which a solute is reduced and precipitated to an oxidation direction; detecting information regarding a current change by using any one of the repeating redox method, the multi-step redox method, and the redox scanning method during an electrolytic reduction process of the non-aqueous electrolyte; and calculating metal ion concentration or oxygen ion concentration in the non-aqueous electrolyte during the electrolytic reduction process by using the correlation and the information regarding the current change.

According to the monitoring apparatus of metal ions or oxygen ions applicable to higher concentration non-aqueous electrolyte, since a change in the electrode area in the non-aqueous solution as in the related art is eliminated, stable electrochemical measurement can be performed in the non-aqueous electrolyte.

Also, according to embodiments of the present invention, a linear relationship between concentration and current can be detected in the non-aqueous electrolyte, while maintaining concentration, by varying an applied potential. Accordingly, concentration and components of a solute existing in a non-aqueous electrolyte can be measured while an electrowinning processing and pyroprocessing of metal are being performed.

Also, according to embodiments of the present invention, as a monitoring method of metal ions or oxygen ions, at least one of the electrochemical repeating redox method, the repeating multimulti-step redox method, the redox scanning method may be applied. Accordingly, concentration of metal ions and oxygen ions of high concentration as well as low concentration in a non-aqueous solution can be monitored in real time.

In addition, since a high oxidation pulse potential is applied periodically to the working electrode to remove an element electrochemically plated on the working electrode, the surface of the electrode can be maintained to be clean, eliminating a change in the electrode area by a plated metal.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from the detailed description.

BRIEF DESCRIPTION OF THE DRAWINGS

The accompanying drawings, which are included to provide a further understanding of the invention and are incorporated in and constitute a part of this specification, illustrate exemplary embodiments and together with the description serve to explain the principles of the invention.

In the Drawings

DETAILED DESCRIPTION OF THE INVENTION

Figure 1:
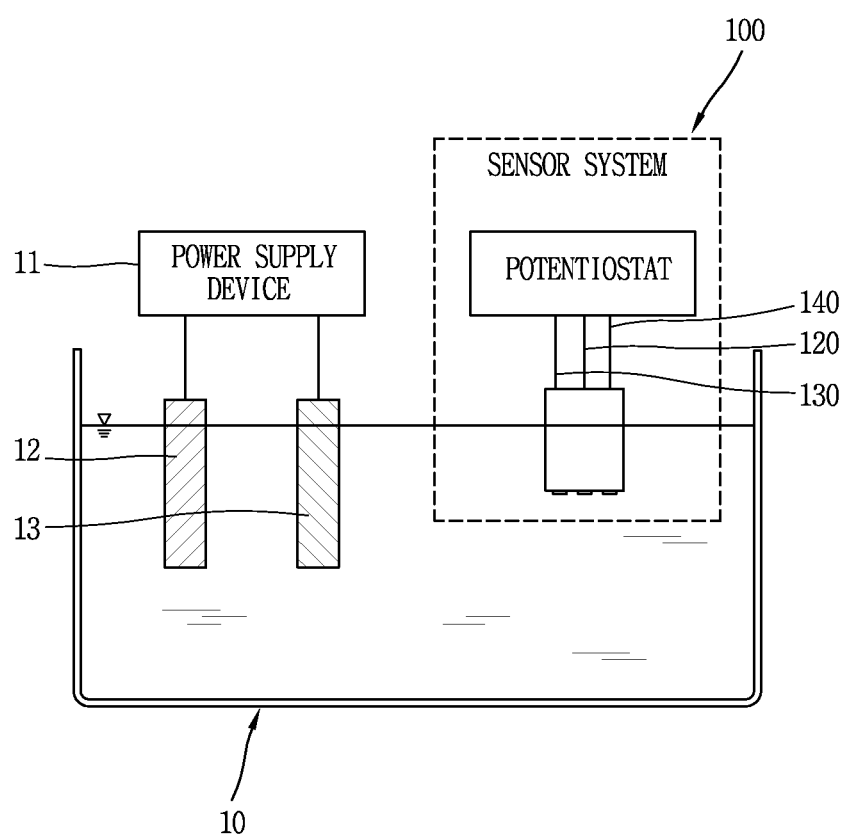
FIG. 1 is a conceptual view of a monitoring apparatus for electrochemically monitoring concentration of a non-aqueous electrolyte in real time according to an embodiment of the present invention.

Description will now be given in detail of the exemplary embodiments, with reference to the accompanying drawings. For the sake of brief description with reference to the drawings, the same or equivalent components will be provided with the same reference numbers, and description thereof will not be repeated.

A monitoring method and system of metal ions or oxygen ions applicable to higher concentration non-aqueous electrolyte in relation to an embodiment of the present invention will be described in detail with reference to the accompanying drawings. In the present disclosure, like and similar reference numerals are used for the like and similar components although embodiments are different, and a description thereof will be replaced by a first description. Also, as used herein, singular forms "a", "an" and "the" are intended to include the plural forms as well, unless the context clearly indicates otherwise.

FIG. 1 is a conceptual view of a monitoring apparatus for electrochemically monitoring a non-aqueous electrolyte in real time online according to an embodiment of the present invention.

Referring to FIG. 1, for a metal electrolytic refining or pyroprocessing apparatus, a process reactor 10 includes a power supply device 11, an anode 12, and a cathode 13. In a metal electrolytic refining or pyroprocessing using such an apparatus, a metal electrodeposition occurs in the cathode 13 of the process reactor 10 to recover metal.

A monitoring apparatus 100 includes a sensor including a potentiostat 110, a reference electrode 120, a working electrode 130, and a counter electrode 140. When the sensor is put in the process reactor 10 while a process is being performed, and the monitoring apparatus 100 may monitor concentration of metal ions and oxygen ions and elements in real time. Namely, the working electrode 130, the counter electrode 140, and the reference electrode 120 are put in a non-aqueous electrolyte of the process reactor 10, in order to obtain information regarding a current measured due to a difference between potentials applied to a working electrode in the non-aqueous electrolyte.

When power is applied from the power supply device 11, a deposit product such as metal, or the like, is deposited on the cathode 13, and at the same time, dissolution reaction of the metals or an electrolytic decomposition reaction occurs in the counter electrode 12. At this time, a current measurement is performed by using the working electrode 130 of a sensor device according to any one of an electrochemical repeating redox method, an electrochemical repeating multi-step redox method, an electrochemical redox scanning method. By appropriately adjusting a potential range of the electrochemical repeating redox method, an electrochemical repeating multi-step redox method, an electrochemical redox scanning method, concentrations and components of metal ions and oxygen ions dissolve in the non-aqueous solution can be measured. In detail, a correlation between concentration and current of the metal ions or oxygen ions may be previously set, and concentration of the metal ions or the oxygen ions may be estimated in the process reactor 10 by using the pre-set correlation and a measured current. In this case, a calculation unit (not shown) may calculate concentration of the metal ions and oxygen ions of the non-aqueous electrolyte during the pyroprocessing of the non-aqueous electrolyte by using the current information with respect to the potential and the concentration of the metal ions or oxygen ions of the non-aqueous electrolyte. Through this method, concentration of the metal ions of the non-aqueous solution of high concentration of 4 wt % or higher can be calculated.

For example, the power supply device 11 varies the potential applied to the concentration of the metal ions or oxygen ions in order to maintain concentration of the metal ions or the oxygen ions of the non-aqueous electrolyte although the potential is being applied in the sensor system 100 and, the calculation unit detects a linear relationship between the concentration and the current in the non-aqueous electrolyte by obtaining the current information with respect to the potential while changing the concentration, and calculates concentration of the metal ions or oxygen ions of the non-aqueous electrolyte by using the linear relationship.

Figure 2:
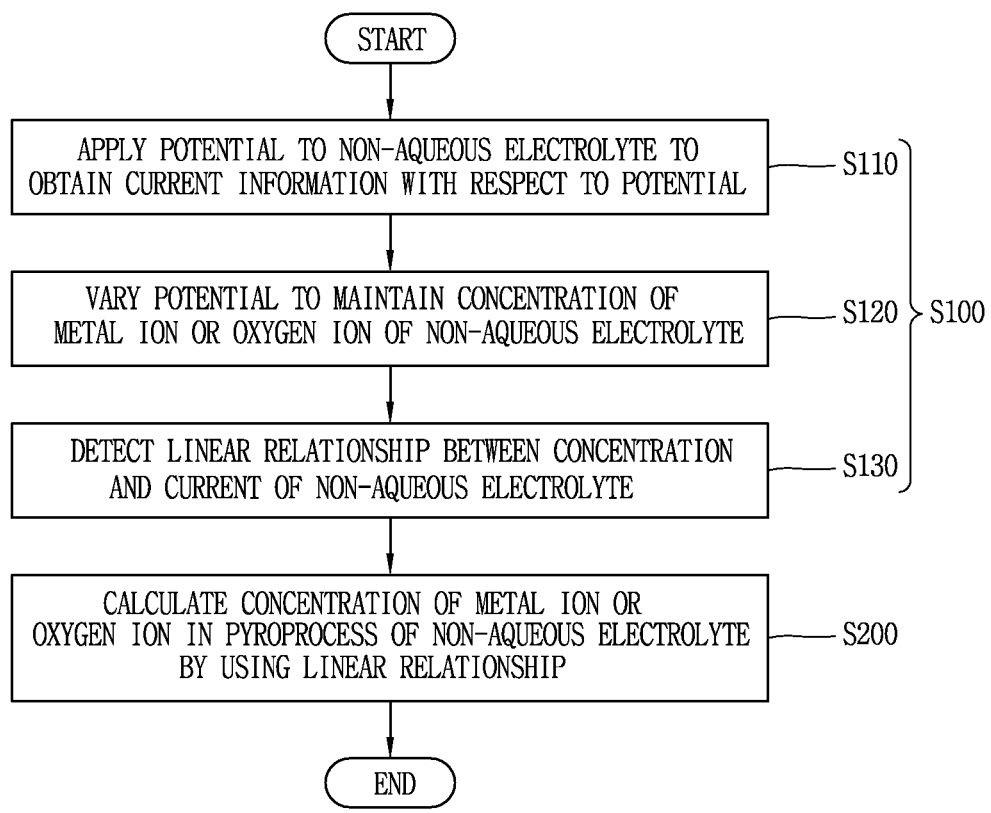
FIG. 2 is a flow chart illustrating a method of monitoring metal ions or oxygen ions applicable to the monitoring apparatus of FIG. 1.

Hereinafter, the monitoring method of metal ions or oxygen ions applicable to higher concentration non-aqueous electrolyte that can be applied to the monitoring apparatus 100 will be described in detail. FIG. 2 is a flow chart illustrating a method of monitoring metal ions or oxygen ions applicable to the monitoring apparatus of FIG. 1.

Referring to FIG. 2, according to the monitoring method, first, a potential is applied to a non-aqueous electrolyte to obtain current information with respect to the potential (S110). The applied potential is varied to maintain the concentration of the metal ions or oxygen ions of the non-aqueous electrolyte although the potential (or the difference of potential) is applied (S120).

Next, step (S110) of obtaining the current information while changing the concentration and the step (S120) of varying the potential are repeatedly performed to obtain a relationship between the concentration and the current in the non-aqueous electrolyte (S130).

Namely, by using any one of the repeating redox method in which periods are repeated by changing a direction of a redox potential, a repeating multi-step redox method in which a potential is changed by stages, and a redox scanning method in which a potential is applied from a reducible point toward oxidation, a potential is applied while changing concentration of the metal ions or oxygen ions in the non-aqueous electrolyte (or molten salt), to obtain a correlation between the potential and the current in each concentration (S100).

Since a positive potential and a negative potential are sequentially applied in the repeating redox method, since an oxidation current and a reduction current are used in turn in the repeating multi-step redox method, and since a current corresponding to reduction is changed into a current corresponding to oxidation in the redox scanning method, although a potential is applied, concentration of the solute can be maintained in a solution/electrode interface.

Thereafter, concentration of the metal ions or oxygen ions of the non-aqueous electrolyte is calculated during the pyroprocessing of the non-aqueous electrolyte by using the linear correlation (S200).

The metal ions may be one selected from the group consisting of lithium (Li), natrium (Na), potassium (K), rubidium (Rb), cesium (Cs), francium (Fr), beryllium (Be), magnesium (Mg), calcium (Ca), strontium (Sr), barium (Ba), radium (Ra), aluminum (Al), silicon (Si), scandium (Sc), titanium (Ti), vanadium (V), chromium (Cr), manganese (Mn), ferrite (Fe), cobalt (Co), nickel (Ni), copper (Cu), zinc (Zn), gallium (Ga), germanium (Ge), arsenic (As), selenium (SE), yttrium (Y), zirconium (Zr), niobium (Nb), molybdenum (Mo), technetium (Tc), ruthenium (Ru), rhodium (Rh), palladium (Pd), silver (Ag), cadmium (Cd), indium (In), tin (Sn), antimony (Sb), tellurium (Re), lanthanum (La), hafnium (Hf), tantalum (Ta), tungsten (W), rhenium (Re), osmium (Os), iridium (Ir), platinum (Pt), gold (Au), mercury (Hg), thallium (Tl), lead (Pb), bismuth (Bi), polonium (Po), actinium (Ac), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), thorium (Th), protactinium (Pa), uranium (U), neptunium (Np), plutonium (Pu), americium (Am), and curium (Cm), or any mixture thereof.

Also, the non-aqueous electrolyte may be one selected from the group consisting of LiCl, KCl, NaCl, RbCl, CsCl, $CaCl_2$, $MgCl_2$, $SrCl_2$, $BaCl_2$, $AlCl_3$, $ThCl_3$, LiF, KF, NaF, RbF, CsCl, $CaF_2$, $MgF_2$, $SrF_2$, $BaF_2$, $AlF_3$, $ThF_3$, acetonitrile, tetrafluoroborate anion, 1-butyl-3-methylimidazolium chloride, 1-butyl-1-methylpyrrolidinium bis(trifluoromethlylsulfonyl)imide, 1-butylpyridinium chloride, choline chloride, 1-butyl-3-methylimidazolium chloride, demethylethylphenylammonium bromide, dimethylformamide, dimethyl sulfone, dimethyl sulfoxide, ethylene carbonate, ethylene-diaminetetra-acetic acid tetrasodium salt, ethlyene glycol, 1-ethyl-3-methylimidazolium cation, 1-octyl-1-methyl-pyrrolidinium bis(trifluoromethylsulfonyl)imide, hexafluorophosphate anion, 1-propyl-3-methylimidazolium chloride, trihexyl-tetradecyl-phosphonium bis(trifluoromethylsulfonyl)imide, tetrabutylammonium chloride bis(trifluoromethylsulfonyl)imide, tetrahydrofuran, trimethylphenylammonium chloride, or any mixture thereof.

In detail, current change information is detected by using any one of the repeating redox method, the repeating multi-step redox method, and the redox scanning method of the electrolytic reduction process of the non-aqueous electrolyte (or molten salt) (S210), and concentration of the metal ions or oxygen ions of the non-aqueous electrolyte (or molten salt) is calculated in the electrolytic reduction process by using the correlation and the current change information (S220).

In this manner, by simultaneously performing the repeating redox method, the repeating multi-step redox method, and the redox scanning method when the process reactor 10 performs the process, concentration of the metal ions or oxygen ions dissolved in the non-aqueous solution can be monitored in real time.

Hereinafter, correlation of current with potential according to the repeating redox method, the repeating multi-step redox method, and the redox scanning method will be described in detail with reference to FIGS. 3 through 12.

Figure 3:
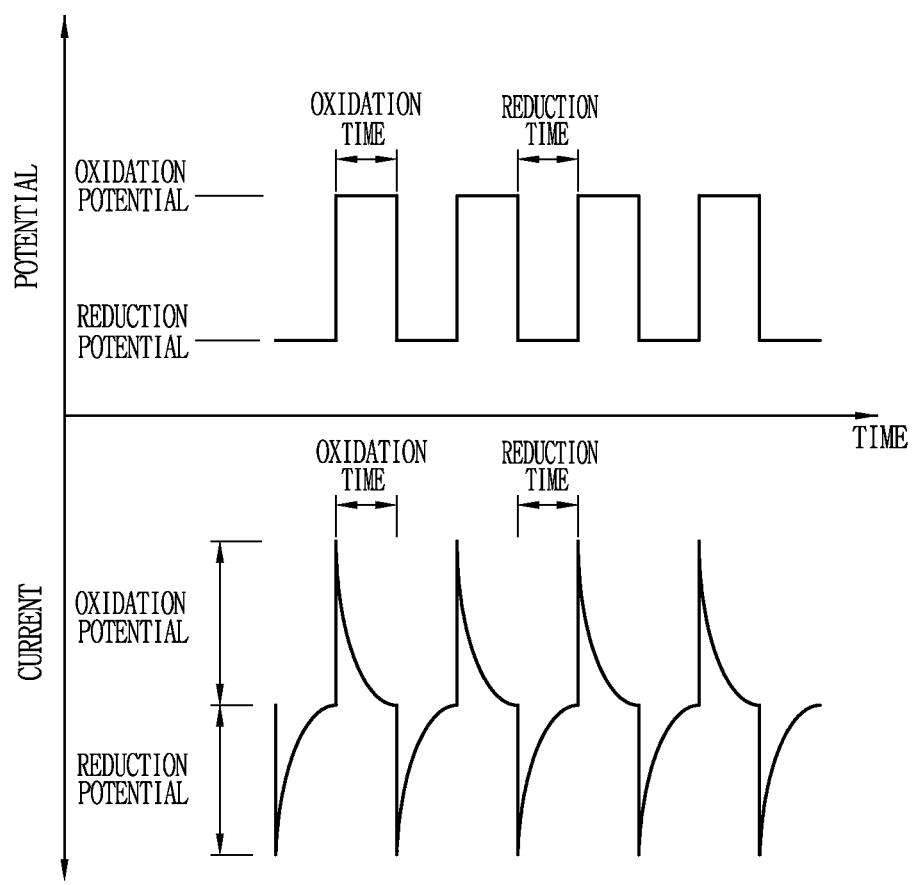
FIG. 3 is a graph showing examples of waveforms of potential and current used in an electrochemical repeating redox method, as temporal functions.

In the case of using the repeating redox method, oxidation and reduction potentials are repeatedly applied in the non-aqueous electrolyte in the obtaining step and the varying step. In particular, the oxidation and reduction potentials having a constant magnitude, respectively, are applied in the non-aqueous electrolyte. In detail, as illustrated in FIG. 3, in the repeating redox method, positive and negative potentials are applied in the non-aqueous electrolyte by stages over time based on oxidation and reduction formal potential of the measured metal ions or oxygen ions, so that when the positive potential is applied, a current according to an electrochemical oxidation of metal ions or oxygen ions is measured, and when the negative potential is applied, a current according to a reduction is measured.

Figure 4:
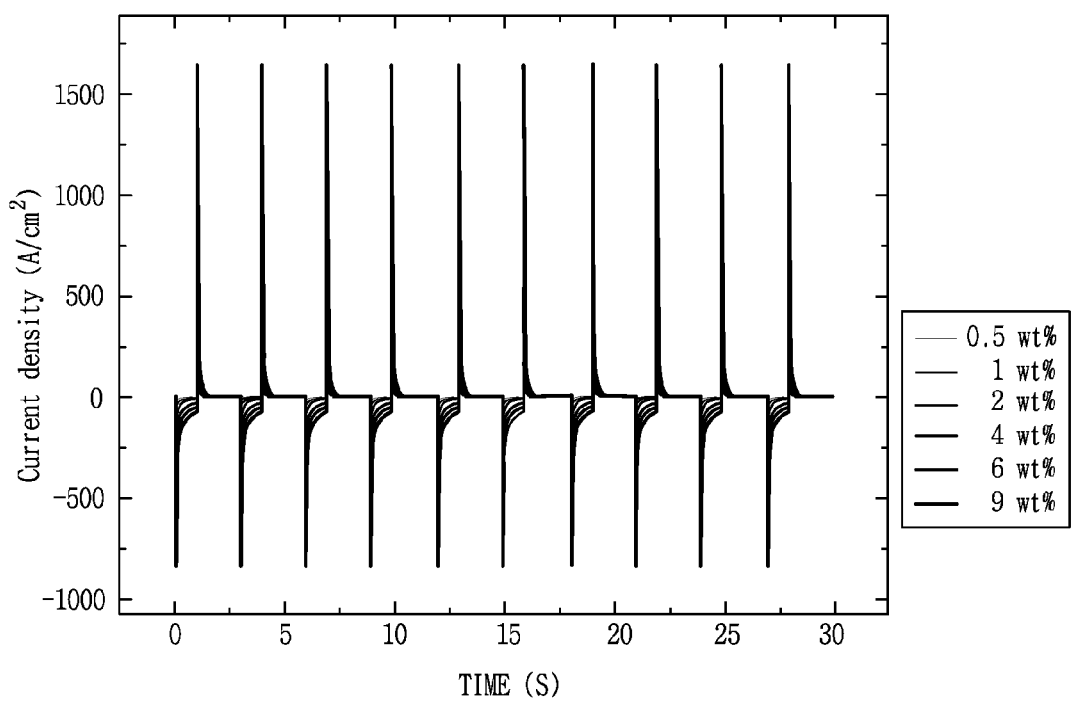
FIG. 4 is a graph showing currents of time slots measured by applying repeating redox potential to molten salt having a high temperature including $NdCl_3$ of various concentrations by using tungsten as a working electrode.

FIG. 4 is a graph showing results of current over time obtained by performing the repeating redox method in a non-aqueous electrolyte with $NdCl_3$ of various concentrations dissolved therein. It can be seen that, when $Nd^{3+}$ has a positive potential relative to an electrodeposition reduction potential, a positive current flows due to oxidation dissociation of electrodeposited Nd in the positive potential, and a negative current flows according to reduction electrodeposition of the Nd metal in a negative potential.

Figure 5:
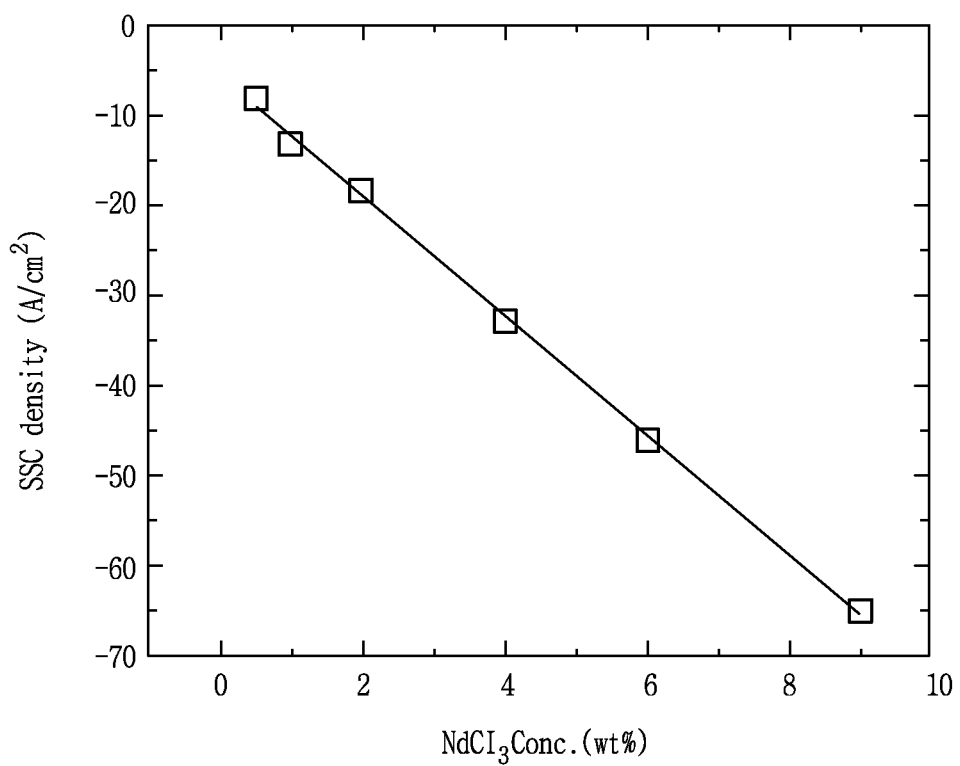
FIG. 5 is a graph showing constant currents of measurement results of an electrochemical repeating redox method of FIG. 4 according to concentration of $NdCl_3$.

FIG. 5 is a graph showing a constant current value as a stabilized current among negative currents measured in FIG. 4 over concentration of $Nd^{3+}$ dissolved in the non-aqueous electrolyte. It can be seen that the constant current value is measured to be linearly proportional to an amount of concentration of a solute dissolved in the electrolyte in all the concentration ranges. According to the results, concentration of the metal ions in the electrolyte can be measured by measuring constant current values.

Figure 6:
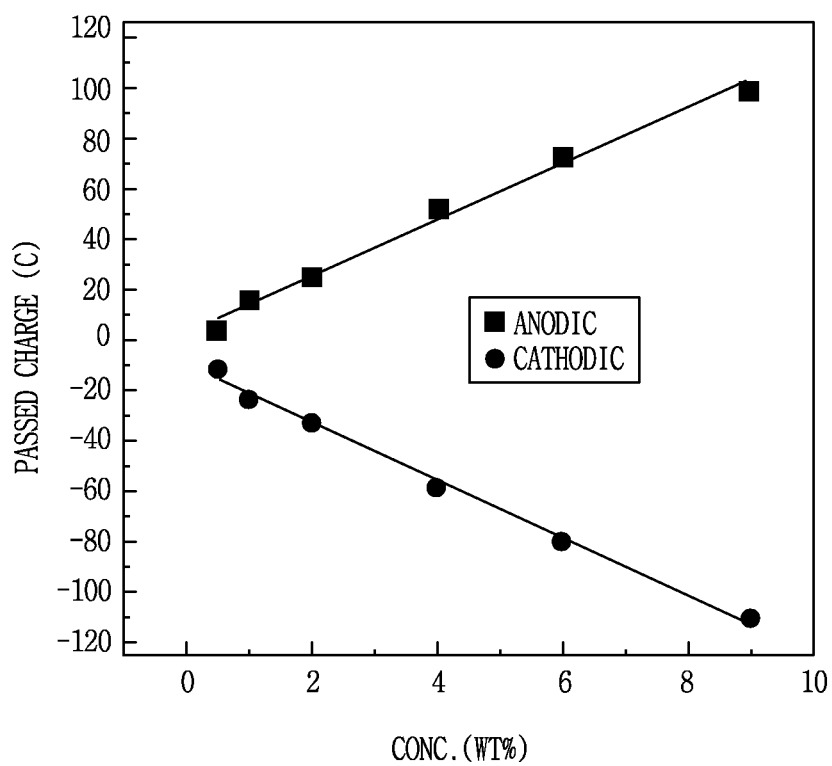
FIG. 6 is a graph showing quantity of passed charge of results of the electrochemical repeating redox method of FIG. 4 according to concentration of $NdCl_3$.

FIG. 6 is a graph showing quantity of passed charges measured by integrating current results measured in FIG. 4, over concentration of the solute dissolved in the non-aqueous electrolyte. It can be seen that the quantity of passed charges participating in the reaction is linearly proportional to the concentration of the solute in the electrolyte. Concentration of the metal ions in the electrolyte can be estimated by measuring a quantity of passed charges flowing therein.

In the case of using the multi-step redox method, the obtaining step and the varying step may be steps in which a potential maintaining a constant magnitude is applied in the non-aqueous electrolyte, while decreasing or increasing it such that a reduction current and an oxidation current are sequentially generated.

Figure 7:
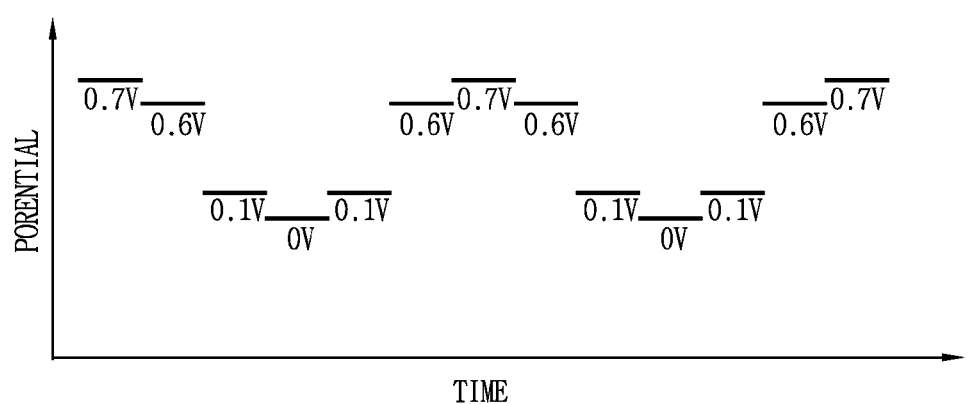
FIG. 7 is a graph showing examples of waveforms of potential used for an electrochemical repeating multi-step redox method, as temporal functions.

As illustrated in FIG. 7, in the repeating multi-step redox method, as an electrochemical potential is applied by stages over time, an oxidation and reduction current of the metal ions or oxygen ions appear in the vicinity of the oxidation and reduction formal potential of the metal ions or oxygen ions.

When a potential below the formal potential is applied, a base current such as charge current of an electrode surface, rather than a kinetic current of target ions, flows, and when an overpotential higher than the formal potential is applied, a current resulting from a reaction of the target ions flows. Since the formal potential of a target material has been already known, a component and concentration of the metal ions and oxygen ions existing in the non-aqueous electrolyte can be measured by measuring a current by adjusting the overpotential.

Figure 8:
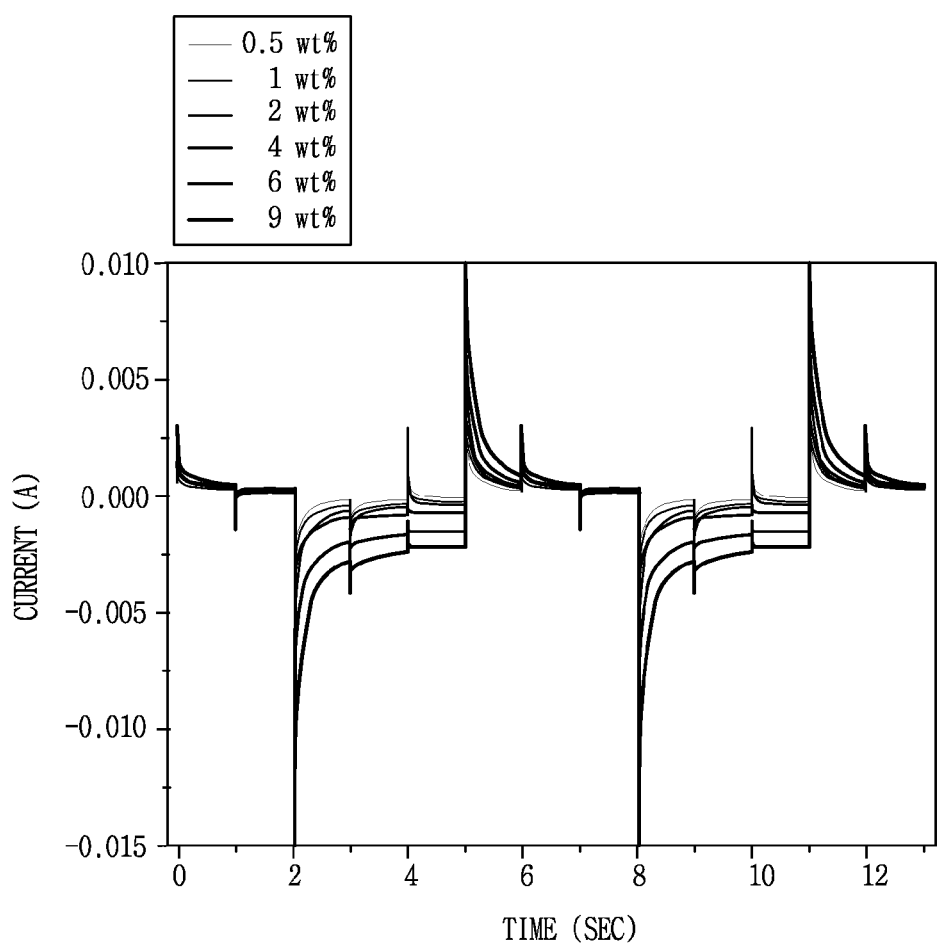
FIG. 8 is a graph showing currents of time slots measured by using tungsten as a working electrode in molten salt having a high temperature including $EuCl_3$ by using the repeating multi-step redox method.

FIG. 8 is a graph showing current over time obtained by performing the repeating multimulti-step redox method by dissolving EuCl2 of various concentrations in a non-aqueous electrolyte. Large reduction current an oxidation current appear between 0.6 V and 0.1 V, which result from oxidation and reduction of $Eu^{2+/3+}$.

Figure 9:
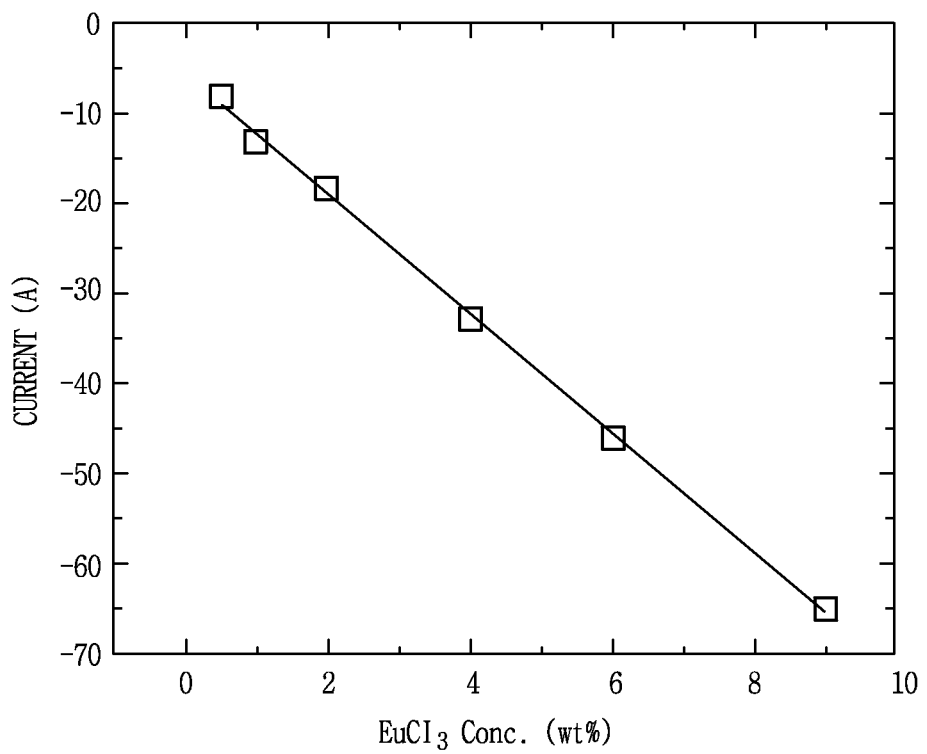
FIG. 9 is a graph showing constant currents of the results of the repeating multi-step redox method of FIG. 7 according to concentrations of $EuCl_3$.

FIG. 9 is a graph showing a constant current, among currents appearing when +0.1V is applied, over concentration of $Eu^{2+}$ dissolved in the non-aqueous. According to the graph, it can be seen that the measured constant current is linearly proportional to concentration of the metal ions, and a constant current may be measured by using the result to thereby measure concentration of the metal ions and oxygen ions existing in the non-aqueous solution.

In the case of using the redox scanning method, the obtaining step and varying step may be replaced by the steps of applying a potential to electrodeposit the metal ions and of increasing a potential to dissolve the electrodeposited metal film, respectively.

Figure 10:
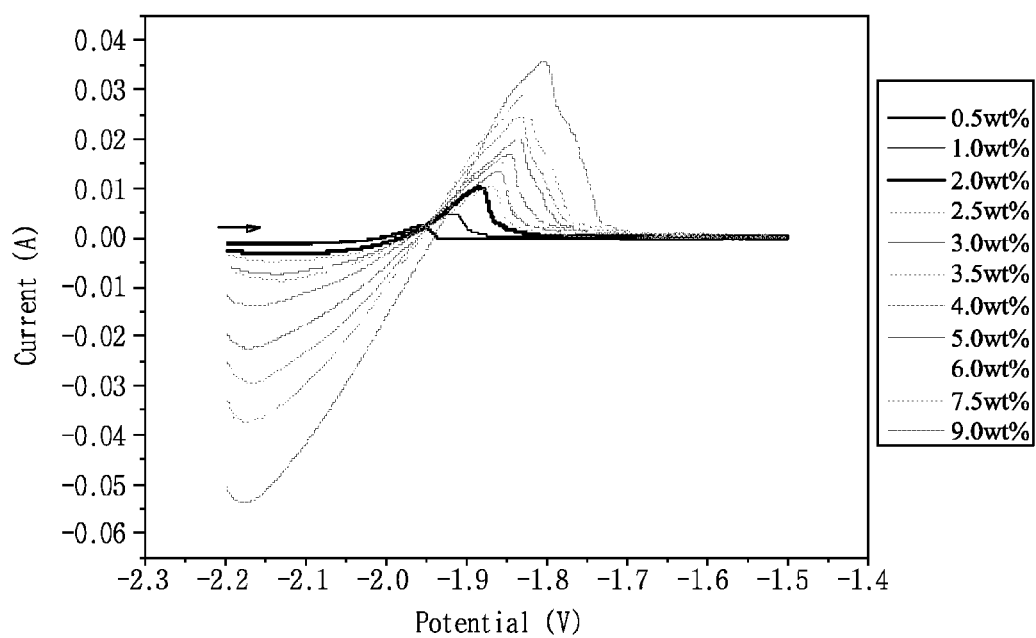
FIG. 10 is a graph showing current over potential measured by using tungsten as a working electrode in molten salt having a high temperature including $NdCl_3$ of various concentrations by using a redox scanning method.

FIG. 10 is a graph showing current data over potential measured by performing the redox scanning method after $Nd^{3+}$ of various concentrations is dissolved in a non-aqueous electrolyte. It can be seen that as the potential applied to the working electrode is shifted from a negative potential to a positive potential, a positive current attributable to the dissolution of the metal is found.

Figure 11:
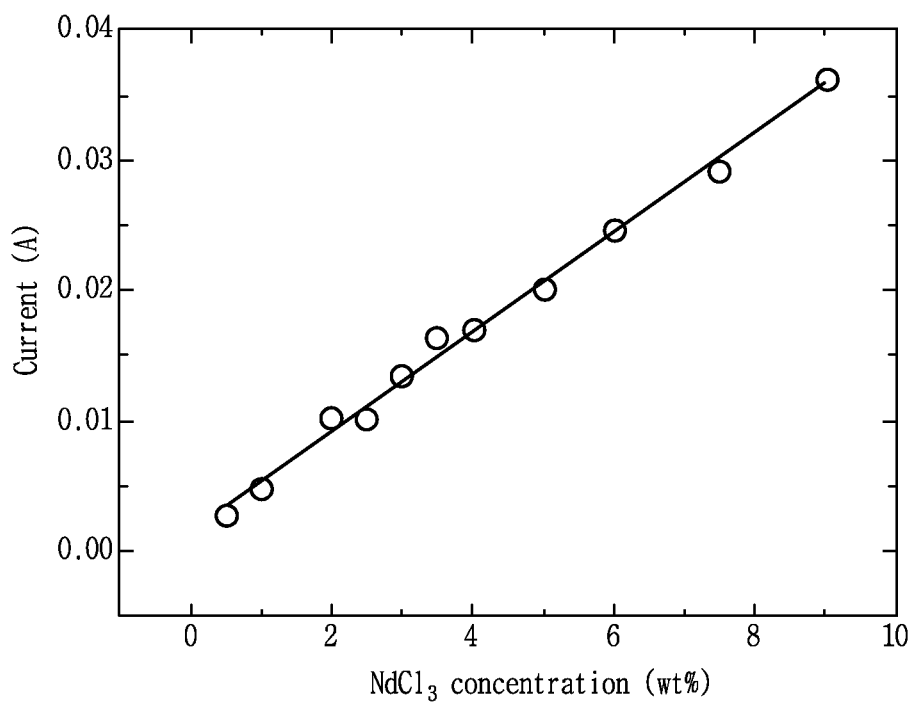
FIG. 11 is a graph showing an oxidation and reduction signal current value over $NdCl_3$ concentration according to the measurement results of redox scanning method of FIG. 10.

FIG. 11 is a graph showing a peak current measured through the electrochemical redox scanning method over concentration of the metal ions. It can be seen that the peak current is linearly proportional to the concentration of the metal ions, and a peak current may be measured by using the corresponding results to thereby measure concentration of the metal ions in the non-aqueous solution.

Figure 12:
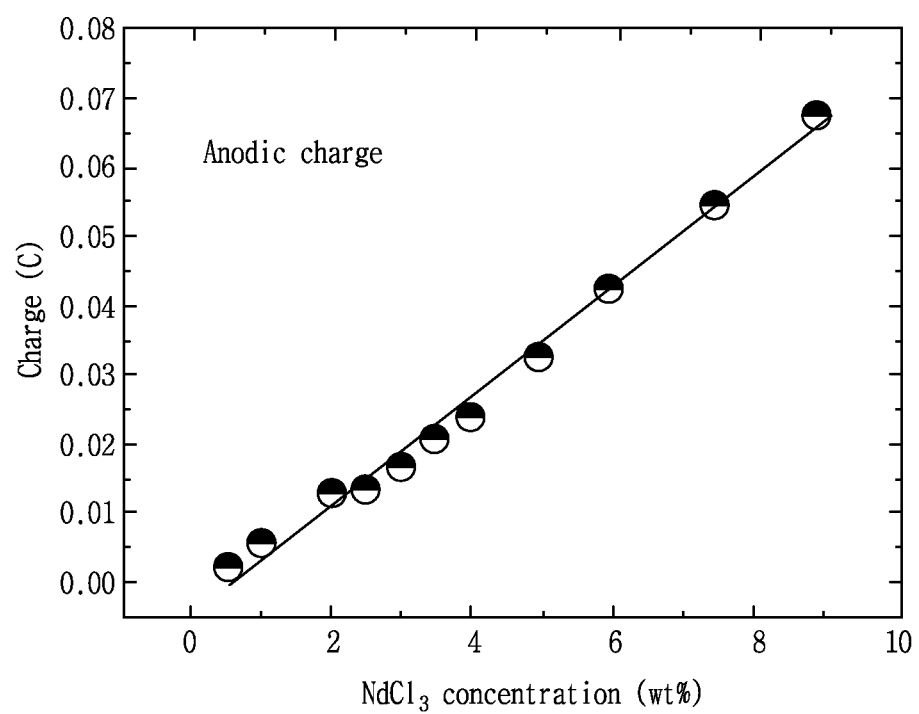
FIG. 12 is a graph showing oxidation and reduction charge amount over $NdCl_3$ concentration according to the measurement results of redox scanning method of FIG. 10.

FIG. 12 is a graph showing a quantity of passed charges obtained by integrating a positive current measured through the redox scanning method in FIG. 10 over concentration of metal ions. It can be seen that the quantity of passed charges is linearly proportional to the concentration of metal ions, and a quantity of passed charges can be measured by using the corresponding result to thereby measure concentration of the metal ions in the non-aqueous solution.

Figure 13:
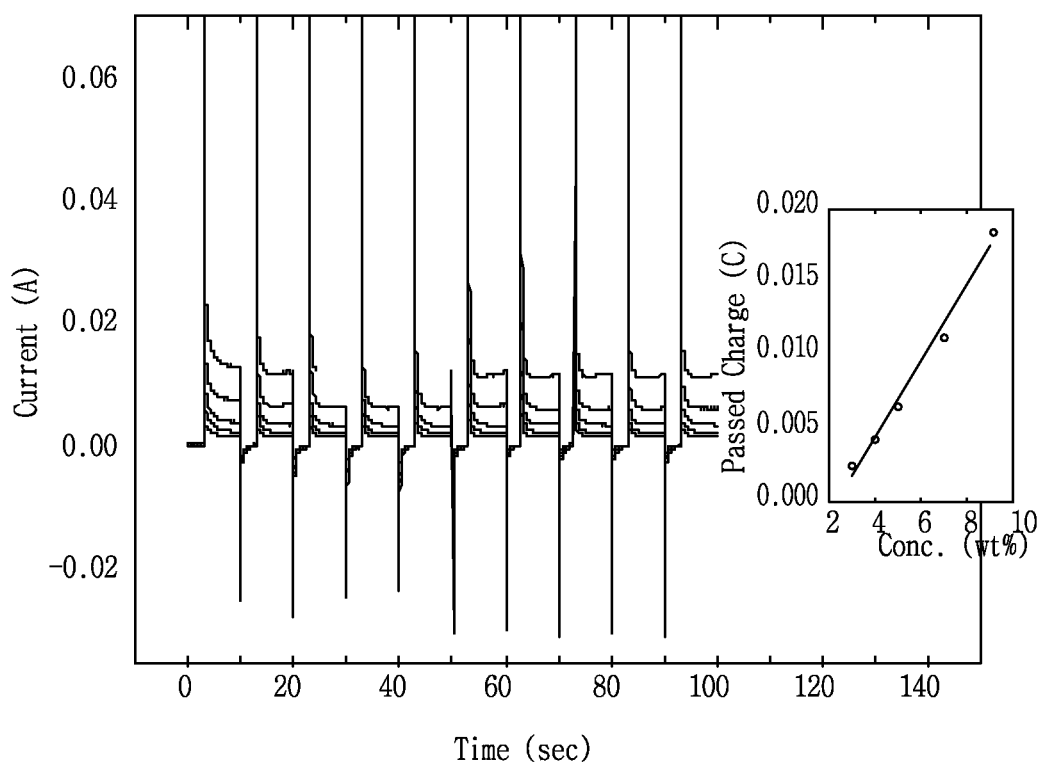
FIG. 13 is a graph showing currents over time slots measured by applying repeating oxidation-reduction potential to molten salt including $Li_2O$ of various concentrations at high temperature by using platinum as a working electrode, and a graph of passed charge over concentration.

FIG. 13 is a graph showing current time over time measured by performing the repeating redox method after dissolving $O^{2-}$ of various concentrations in a non-aqueous electrolyte and a graph showing an quantity of passed charges over concentration. Oxygen ions are oxidized at a positive potential, and then a negative potential is applied to reduce evolved oxygen gas or make it disappear in the bulk of the solution, thereby accurately measure concentration of the oxygen ions in the non-aqueous solution by using the current and the quantity of passed charges.

Figure 14:
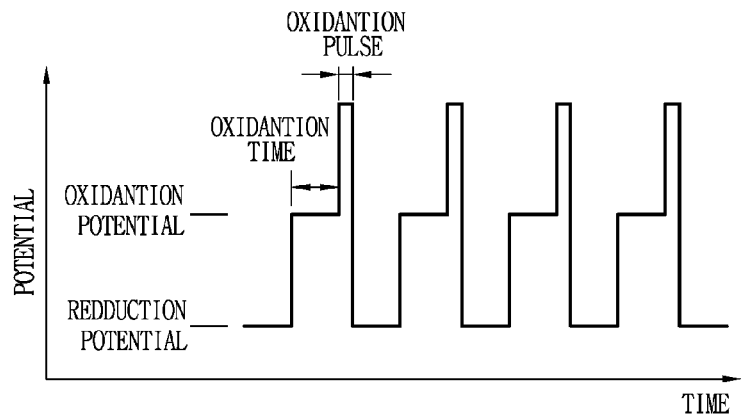
FIG. 14 is a graph showing waveforms of potential obtained by applying positive potential pulse to the waveform of FIG. 5 in order to maintain a clean surface of a working electrode by a time function.

FIG. 14 is a graph showing waveforms of potential obtained by applying positive potential pulse to the waveform of FIG. 3 in order to maintain cleanliness of the surface of a working electrode, by a time function. Namely, a pulse potential equal to or higher than 0V (vs. Ag|AgCl) may be applied to the working electrode periodically. Thus, by removing an electrochemically plated deposit, a change in the electrode area due to a electrodeposited metal is prevented and a surface of the electrode is maintained to be clean. In this case, the area of the working electrode may be equal to or smaller than 0.5 $cm^2$. For example, the area of the working electrode may range from 1 $nm^2$ to 0.5 $cm^2$. Also, a magnitude of the pulse potential may range from 0V to 100V. In this case, a positive pulse potential equal to or higher than 0V may be applied periodically to the working electrode to allow the surface of the electrode to be clean and have a constant area.

The monitoring system may employ the foregoing monitoring method and any other methods for making the electrode area constant may be used in non-aqueous electrolyte.

Figure 15:
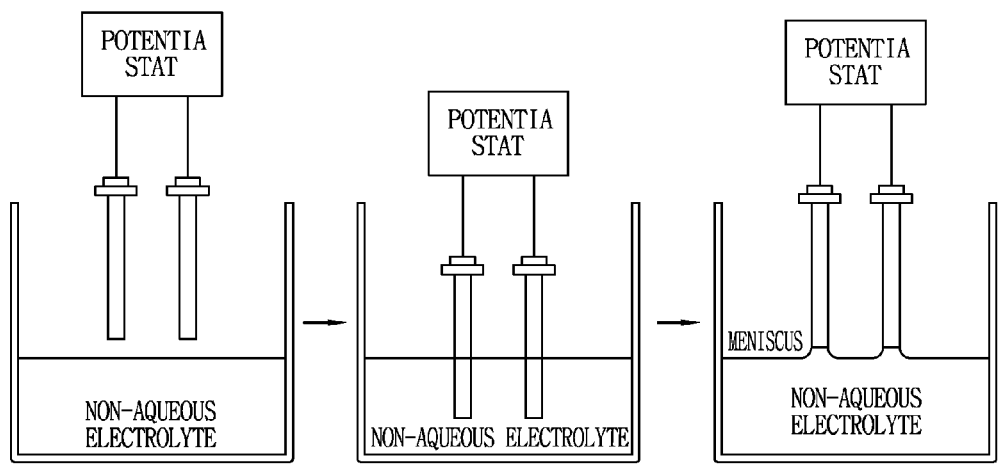
FIG. 15 is a conceptual view of a meniscus formed by putting an electrode in an electrolyte and raising it therefrom, in order to constantly maintain an electrode area.
Figure 16:
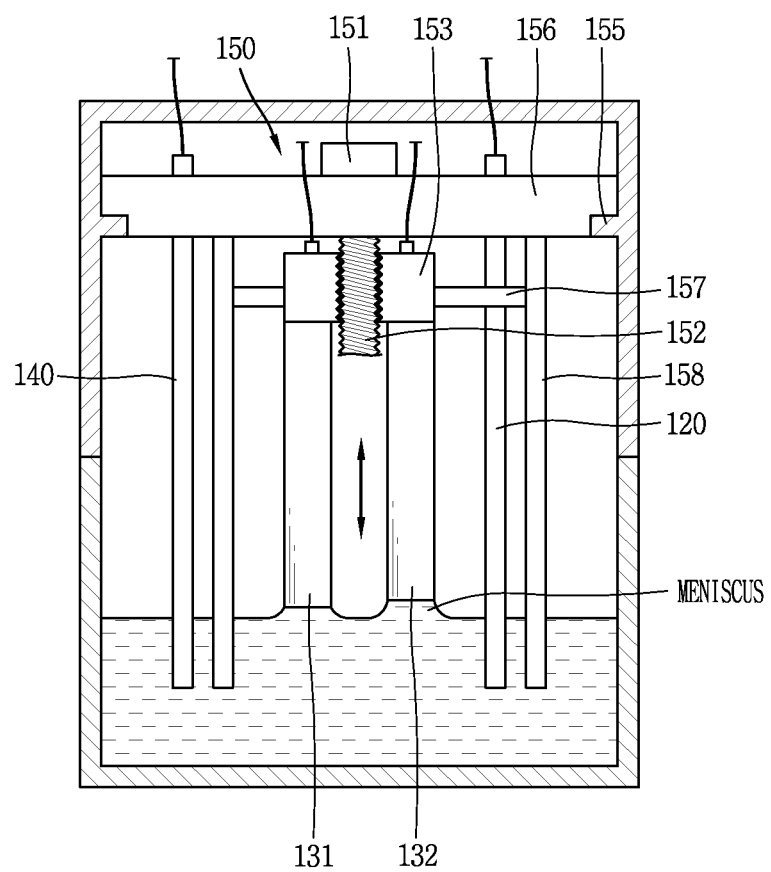
FIG. 16 is a view illustrating a configuration of a monitoring system for forming the meniscus.

FIG. 15 is a conceptual view of a meniscus formed by putting an electrode in an electrolyte and raising it therefrom, in order to uniformly maintain an electrode area. FIG. 16 is a view illustrating a configuration of a monitoring system for forming the meniscus.

As mentioned above, it is difficult to maintain an electrode constantly in the non-aqueous electrolyte. Thus, in order to resolve the problem, when the electrode is put in the electrolyte as illustrated in FIG. 15 and raised therefrom, a meniscus is formed due to surface tension of the electrolyte. When the electrode is allowed to be in contact with the electrolyte in this manner, an electrode area may be limited to a lower portion of the electrode constantly in contact with the solution.

Referring to FIG. 16, the monitoring system includes an adjusting device 150 in addition to the power supply device, the sensor device, and the calculation unit described with reference to FIG. 1.

The adjusting device 150 is configured to adjust a height of the working electrode 130 by raising the working electrode 130 in a state of being put in a non-aqueous electrolyte to form a meniscus. In detail, the adjusting device 150 includes a driving motor 151, a screw 152, and a nut 153.

A main body 156 is disposed in a direction perpendicular to the working electrode 130 in a port 155 formed in an upper portion of the device, and the driving motor 151 is installed in the main body 156. The driving motor 151 includes a rotational shaft, and a screw 152 is connected to the rotational shaft. In this case, the screw 152 is disposed to be parallel to the working electrode 130.

The nut 153 is connected to a holder 157 for a working electrode and the screw 152, respectively, and thus, when the rotational shaft rotates, the nut 153 moves the working electrode up and down.

Also, a plurality of working electrodes 130 may be provided in both sides of the screw 152 based on the screw 152. Namely, the working electrodes 130 may include a first electrode 131 forming the meniscus on the surface of the non-aqueous electrolyte and a second electrode 132 have a difference in height from the first electrode 131 in order to estimate a height by which the meniscus is formed.

In addition, the adjusting device may include a protective cover 158 covering the working electrode 130 to protect the meniscus formed on the working electrode 130.

Figure 17:
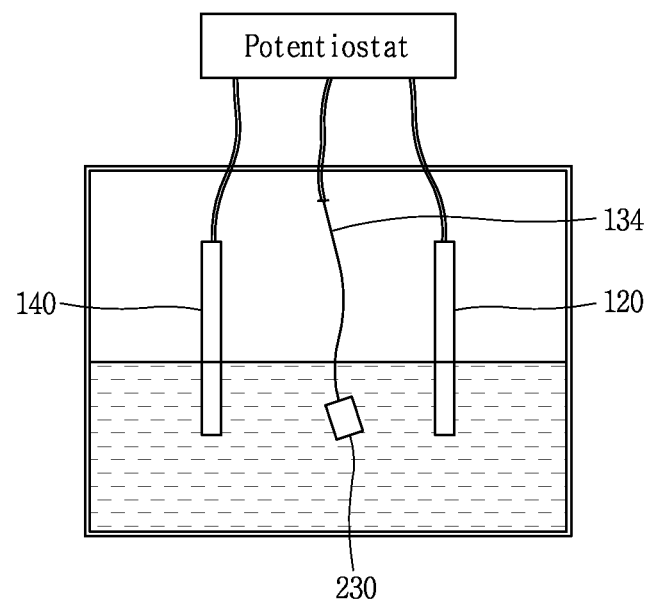
FIG. 17 is a conceptual view of a working electrode connected to a wire in order to constantly maintain an electrode area.

In order to constantly maintain the electrode area, the device may be changed to have a different form. FIG. 17 is a conceptual view of a working electrode connected to a wire in order to constantly maintain an electrode area, and FIG. 18 is a conceptual view of a working electrode covered with MgO and BeO in order to constantly maintain an electrode area.

Referring to FIG. 17, the adjusting device may include a working electrode 230 immersed in the non-aqueous electrolyte and connected to a potentiostat by a wire 134, in order to reduce a relative electrode change.

Figure 18:
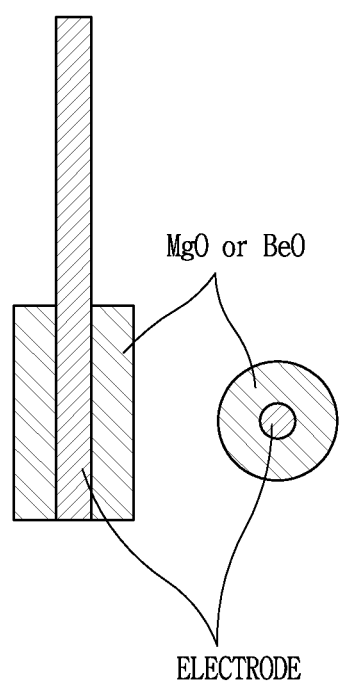
FIG. 18 is a conceptual view of a working electrode insulated by using MgO and BeO to constantly maintain an electrode area.

Referring to FIG. 18, a working electrode which uses MgO or BeO not reactive in the non-aqueous solution, as an insulator covering the electrode immersed in the non-aqueous solution may be provided.

In detail, the working electrode 230 connected to a thin wire 135 having a size equal to or smaller than 1 mm as a means for maintaining the electrode area constantly in the non-aqueous solution is immersed in the non-aqueous solution, whereby a relative electrode change is minimized. Accordingly, the electrode area can be maintained in monitoring the non-aqueous metal ions in real time.

The monitoring method and monitoring system of the metal ions or oxygen ions applicable to higher concentration non-aqueous electrolyte are not limited to the foregoing embodiments and the entirety or a portion of the respective embodiments may be selectively combined to be configured.

The foregoing embodiments and advantages are merely exemplary and are not to be considered as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds are therefore intended to be embraced by the appended claims.

The invention claimed is:

1. A method to monitor the concentration of metal ions or oxygen ions in a non-aqueous electrolyte, the method comprising:
   a first step of applying a constant potential to a working electrode put in said non-aqueous electrolyte to measure the current with respect to the constant potential;
   a second step of varying the constant potential between an oxidation potential and a reduction potential applied to the working electrode while maintaining the concentration of the metal ions or oxygen ions in the non-aqueous electrolyte;
   a third step of detecting a linear relationship between the concentration of the metal ions or oxygen ions in the non-aqueous electrolyte and the current by repeatedly performing the first step and the second step, wherein the concentration of the metal ions or oxygen ions is changed each time a combination of the first step and the second step is repeated; and
   a fourth step of calculating the concentration of the metal ions or oxygen ions in the non-aqueous electrolyte in pyroprocessing of the non-aqueous electrolyte by using the linear relationship;
   wherein a reduction potential having a constant magnitude and an oxidation potential having a constant magnitude are repeatedly applied to the working electrode in the first step and the second step.

2. The method of claim 1, wherein the working electrode, a counter electrode, and a reference electrode of a potentiostat are put in the non-aqueous electrolyte in order to measure the current with respect to the potential.

3. The method of claim 2, wherein in order to maintain cleanliness, a positive pulse potential is further applied periodically to the working electrode.

4. The method of claim 2, wherein in order to form a meniscus to constantly maintain an area of the working electrode in contact with the non-aqueous electrolyte, the working electrode is raised to the surface of the non-aqueous electrolyte.

5. The method of claim 1, wherein the metal ions are one selected from the group consisting of lithium (Li), natrium (Na), potassium (K), rubidium (Rb), cesium (Cs), francium (Fr), beryllium (Be), magnesium (Mg), calcium (Ca), strontium (Sr), barium (Ba), radium (Ra), aluminum (Al), silicon (Si), scandium (Sc), titanium (Ti), vanadium (V), chromium (Cr), manganese (Mn), ferrite (Fe), cobalt (Co), nickel (Ni), copper (Cu), zinc (Zn), gallium (Ga), germanium (Ge), arsenic (As), selenium (SE), yttrium (Y), zirconium (Zr), niobium (Nb), molybdenum (Mo), technetium (Tc), ruthenium (Ru), rhodium (Rh), palladium (Pd), silver (Ag), cadmium (Cd), indium (In), tin (Sn), antimony (Sb), tellurium (Re), lanthanum (La), hafnium (Hf), tantalum (Ta), tungsten (W), rhenium (Re), osmium (Os), iridium (Ir), platinum (Pt), gold (Au), mercury (Hg), thallium (Tl), lead (Pb), bismuth (Bi), polonium (Po), actinium (Ac), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), thorium (Th), protactinium (Pa), uranium (U), neptunium (Np), plutonium (Pu), americium (Am), and curium (Cm), or any mixture thereof.

6. The method of claim 1, wherein the non-aqueous electrolyte is one selected from the group consisting of LiCl, KCl, NaCl, RbCl, CsCl, $CaCl_2$, $MgCl_2$, $SrCl_2$, $BaCl_2$, $AlCl_3$, $ThCl_3$, LiF, KF, NaF, RbF, CsCl, $CaF_2$, $MgF_2$, $SrF_2$, $BaF_2$, $AlF_3$, $ThF_3$, acetonitrile, tetrafluoroborate anion, 1-butyl-3-methylimidazolium chloride, 1-butyl-1-methylpyrrolidinium bis(trifluoromethlylsulfonyl)imide, 1-butylpyridinium chloride, choline chloride, 1-butyl-3-methylimidazolium chloride, demethylethylphenyl-ammonium bromide, dimethylformamide, dimethyl sulfone, dimethyl sulfoxide, ethylene carbonate, ethylene-diamine-tetra-acetic acid tetrasodium salt, ethlyene glycol, 1-ethyl-3-methylimidazolium cation, 1-octyl-1-methyl-pyrrolidinium bis(trifluoromethylsulfonyl)imide, hexafluorophosphate anion, 1-propyl-3-methylimidazolium chloride, trihexyl-tetradecyl-phosphonium bis(trifluoromethylsulfonyl)imide, tetrabutylammonium chloride bis(trifluoromethylsulfonyl) imide, tetrahydrofuran, trimethylphenylammonium chloride, or any mixture thereof.

7. A method to monitor the concentration of metal ions or oxygen ions in a non-aqueous electrolyte, the method comprising:
  a first step of applying a constant potential to a working electrode put in said non-aqueous electrolyte to measure the current with respect to the constant potential;
  a second step of varying the constant potential between an oxidation potential and a reduction potential applied to the working electrode while maintaining the concentration of the metal ions or oxygen ions in the non-aqueous electrolyte;
  a third step of detecting a linear relationship between the concentration of the metal ions or oxygen ions in the non-aqueous electrolyte and the current by repeatedly performing the first step and the second step, wherein the concentration of the metal ions or oxygen ions is changed each time a combination of the first step and the second step is repeated; and
  a fourth step of calculating the concentration of the metal ions or oxygen ions in the non-aqueous electrolyte in pyroprocessing of the non-aqueous electrolyte by using the linear relationship;
  wherein when repeating the first and second steps, a constant potential is applied to the working electrode the magnitude of the constant potential is increased or decreased by stages, in order to sequentially measure a reduction current and an oxidation current.

8. The method of claim 7, wherein a working electrode, a counter electrode, and a reference electrode of a potentiostat are put in the non-aqueous electrolyte in order to obtain information of the current with respect to the potential.

9. A method to monitor the concentration of metal ions or oxygen ions in a non-aqueous electrolyte, the method comprising:
  a first step of applying a potential to a working electrode put in said non-aqueous electrolyte to measure the current with respect to the potential;
  a second step of varying a potential applied to the working electrode while maintaining the concentration of the metal ions or oxygen ions in the non-aqueous electrolyte;
  a third step of detecting a linear relationship between the concentration of the metal ions or oxygen ions in the non-aqueous electrolyte and the current by repeatedly performing the first step and the second step, wherein the concentration of the metal ions or oxygen ions is changed each time a combination of the first step and the second step is repeated; and
  a fourth step of calculating the concentration of the metal ions or oxygen ions in the non-aqueous electrolyte in pyroprocessing of the non-aqueous electrolyte by using the linear relationship;
  wherein in the first step and the second step, a potential allowing for the metal ions to be reduced is applied in the non-aqueous electrolyte to precipitate the metal ions, and the potential is subsequently increased to dissolve the metal ions, and
  wherein in order to form a meniscus to constantly maintain an area of the working electrode in contact with the non-aqueous electrolyte, the working electrode is raised to the surface of the non-aqueous electrolyte.

10. The method of claim 9, wherein an area of the working electrode in contact with the non-aqueous electrolyte has a size ranging from 1 $nm^2$ to 0.5 $cm^2$.

11. The method of claim 9, wherein the working electrode, a counter electrode, and a reference electrode of a potentiostat are put in the non-aqueous electrolyte in order to obtain information of the current with respect to the potential.

12. A monitoring method of metal ions and oxygen ions comprising:
  applying a potential while changing concentration of a solute in a non-aqueous electrolyte to obtain a correlation of a current with the potential in each concentration, by using any one of a repeating redox method in which a reduction potential having a constant magnitude and an oxidation potential having a constant magnitude are repeatedly applied, a multi-step redox method in which a constant potential is changed by stages, and a redox scanning method in which a potential is changed from a potential in which a solute is reduced and precipitated to an oxidation direction;
  detecting information regarding a current change by using any one of the repeating redox method, the multi-step redox method, and the redox scanning method during an electrolytic reduction process of the non-aqueous electrolyte; and
  calculating metal ions concentration or oxygen ions concentration in the non-aqueous electrolyte during the electrolytic reduction process by using the correlation and the information regarding the current change.

13. The method of claim 12, wherein a working electrode, a counter electrode, and a reference electrode of a potentiostat are put in the non-aqueous electrolyte in order to obtain current information with respect to the potential, and a pulse potential ranging from 0V to 100V is periodically applied to the working electrode.

14. A monitoring system comprising:

a power supply device including an oxidation electrode and a reduction electrode to apply a potential in a non-aqueous electrolyte;

a sensor device having a working electrode, a counter electrode, and a reference electrode put in the non-aqueous electrolyte to obtain current information with respect to the potential, and a potentiostat connected to the working electrode, the counter electrode, and the reference electrode;

an adjusting device configured to raise the working electrode to adjust a height of the working electrode to form a meniscus with the non-aqueous electrolyte; and a calculation unit configured to calculate concentration of metal ions or oxygen ions of the non-aqueous electrolyte during pyroprocessing of the non-aqueous electrolyte by using a linear relationship between the concentration of the metal ions or oxygen ions in the non-aqueous electrolyte and the current.

15. The monitoring system of claim 14, wherein the working electrode includes a first electrode forming the meniscus on a surface of the non-aqueous electrolyte and a second electrode having a height difference from the first electrode in order to estimate a height at which the meniscus is formed.

16. The monitoring system of claim 15, further comprising: a protective cover covering the working electrode to protect the meniscus formed on the working electrode.

17. The monitoring system of claim 14, wherein the working electrode is put in the non-aqueous electrolyte and connected to the potentiostat by a wire, in order to reduce a relative electrode area change.

18. The monitoring system of claim 14, wherein the working electrode is insulated by MgO or BeO that does not react in the non-aqueous solution, in order to reduce a relative electrode area change.

19. The monitoring system of claim 14, wherein the adjusting device comprises:

a driving motor having a rotational shaft;

a screw connected to the rotational shaft and disposed to be parallel to the working electrode; and a nut connected to the screw and the working electrode and moving the working electrode according to a rotation of the rotational shaft.

20. The monitoring system of claim 14, wherein the power supply device varies the potential being applied to the working electrode between an oxidation potential and a reduction potential while the concentration of the metal ions or oxygen ions of the non-aqueous electrolyte is maintained, and the calculation unit obtains current information with respect to the potential, while changing the concentration, to detect a linear relationship between the concentration and the current in the non-aqueous electrolyte, and calculates concentration of the metal ions and oxygen ions of the non-aqueous electrolyte by using the linear relationship.

\* \* \* \* \*

UNITED STATES PATENT AND TRADEMARK OFFICE
CERTIFICATE OF CORRECTION

PATENT NO. : 9,291,595 B2
APPLICATION NO. : 13/797401
DATED : March 22, 2016
INVENTOR(S) : Sang Eun Bae et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 667 days.

Signed and Sealed this
Twenty-sixth Day of July, 2016

Michelle K. Lee
*Director of the United States Patent and Trademark Office*